United States Patent [19]

Darfler

[11] Patent Number: 5,466,507
[45] Date of Patent: Nov. 14, 1995

[54] HIGH THERMAL CONDUCTIVITY NON-METALLIC HONEYCOMB WITH LAMINATED CELL WALLS

[75] Inventor: Stephen C. Darfler, Castro Valley, Calif.

[73] Assignee: Hexcel Corporation, Pleasanton, Calif.

[21] Appl. No.: 136,957

[22] Filed: Oct. 14, 1993

[51] Int. Cl.$^6$ ................................................ B32B 3/12
[52] U.S. Cl. ........................ 428/116; 52/793.1; 428/118; 428/367
[58] Field of Search .............................. 428/73, 116, 117, 428/118, 367, 902; 52/806; 156/292

[56] References Cited

U.S. PATENT DOCUMENTS

| | | | |
|---|---|---|---|
| 3,706,614 | 12/1972 | Kirkpatrick et al. | 428/378 X |
| 4,280,926 | 7/1981 | Abe et al. | 428/116 X |
| 4,305,559 | 12/1981 | Jackson | 428/116 X |
| 4,366,085 | 12/1982 | Ikegami et al. | 428/116 X |
| 4,459,976 | 7/1984 | Speros | 126/674 |
| 4,609,820 | 9/1986 | Miyamoto | 428/118 X |
| 4,628,001 | 12/1986 | Sasaki et al. | 428/367 |
| 4,781,994 | 11/1988 | Enoki et al. | 428/703 |
| 4,791,910 | 12/1988 | Ishida et al. | 428/116 X |
| 4,973,963 | 11/1990 | Kurosawa et al. | 428/118 X |
| 4,983,457 | 1/1991 | Hino et al. | 428/367 |
| 5,021,283 | 6/1991 | Takenaka et al. | 428/252 X |
| 5,139,596 | 8/1992 | Fell | 156/292 X |
| 5,218,810 | 6/1993 | Isley, Jr. | 52/725 |
| 5,288,537 | 2/1994 | Corden | 428/116 |

*Primary Examiner*—Henry F. Epstein
*Attorney, Agent, or Firm*—Poms, Smith, Lande & Rose

[57] ABSTRACT

A non-metallic honeycomb structure wherein the thermal conductivity of the structure is increased by incorporating high thermal conductivity pitch-based carbon fibers into the non-metallic resin matrix. In addition to increasing thermal conductivity, the pitch-based carbon fibers are utilized to provide controlled directional heat conductance through the honeycomb structure. In a preferred exemplary embodiment, the cell walls are formed from a plurality of non-metallic unidirectional fabric layers, at least one of which consists essentially of unidirectionally oriented high thermal conductivity fibers.

10 Claims, 4 Drawing Sheets

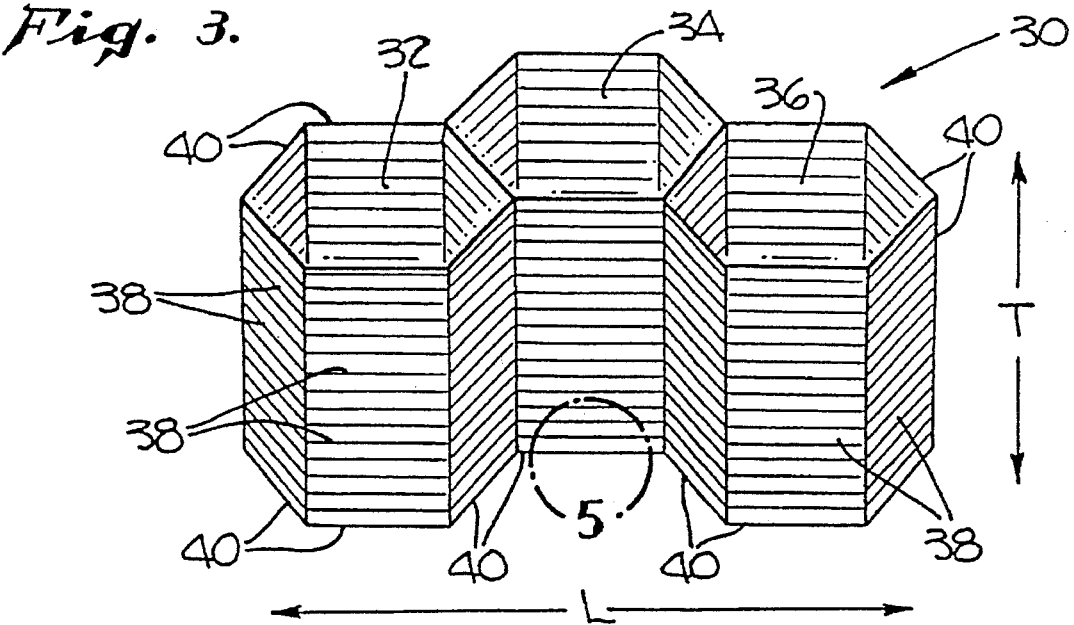
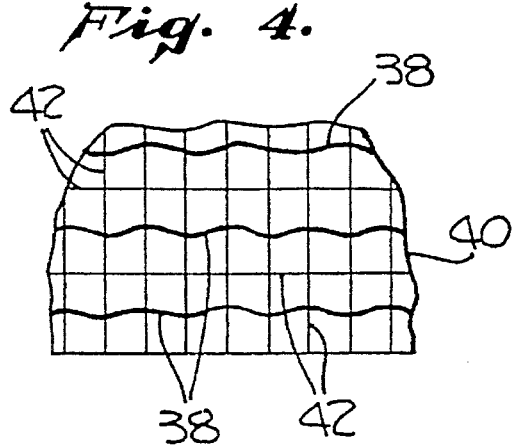
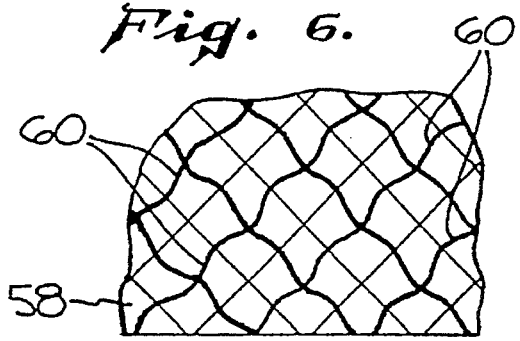
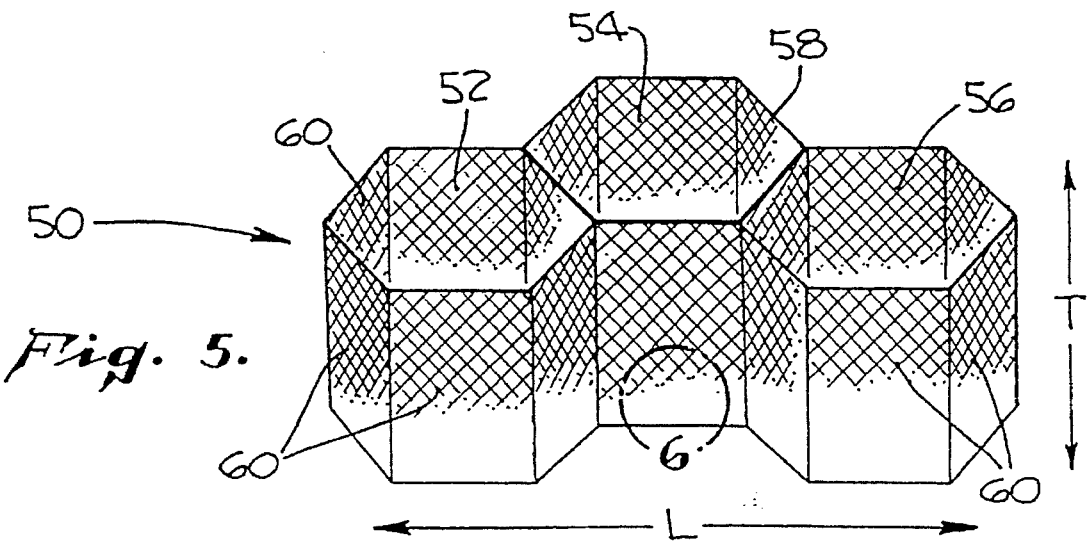

Fig. 10.
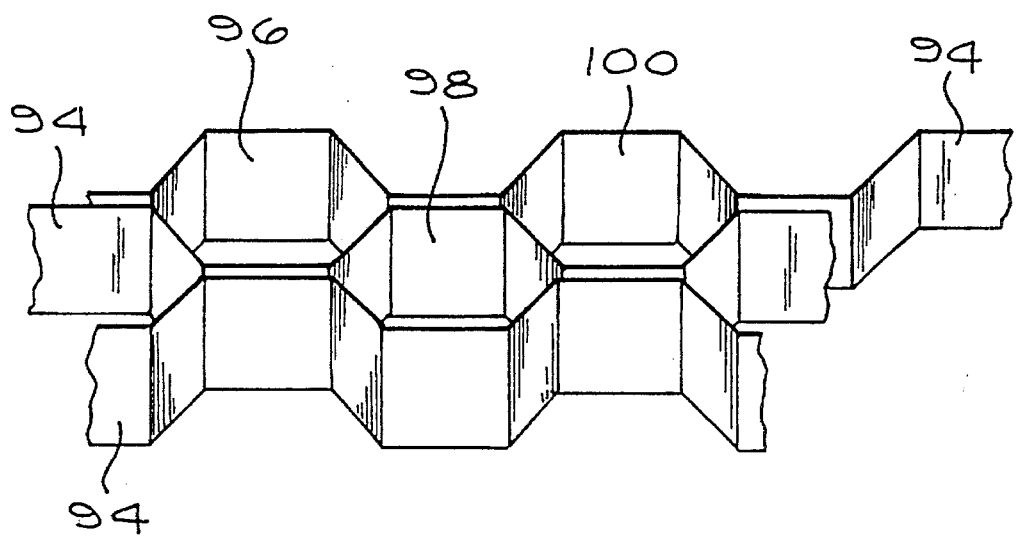
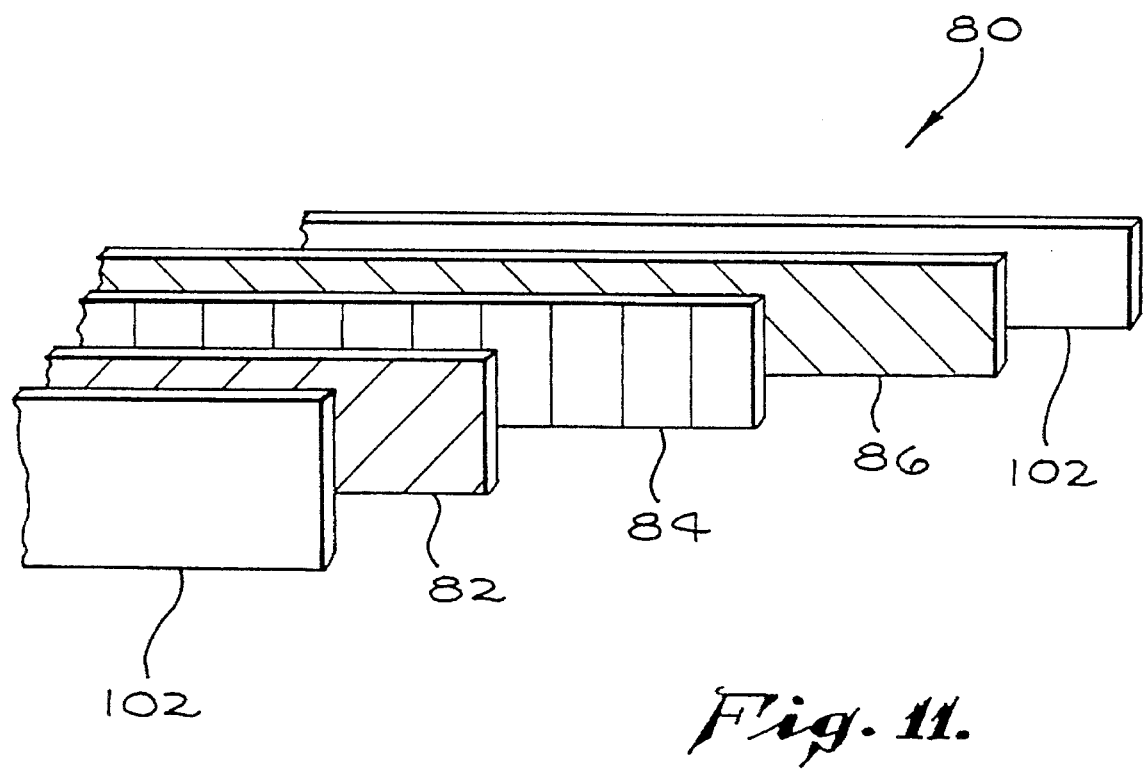
Fig. 11.

HIGH THERMAL CONDUCTIVITY NON-METALLIC HONEYCOMB WITH LAMINATED CELL WALLS

BACKGROUND OF THE INVENTION

1. Field of the Invention

The present invention relates generally to non-metallic honeycomb structures for use in situations where high thermal conductivity through the structure is required. More particularly, the present invention relates to improving the thermal conductivity of non-metallic honeycombs made from composite materials by including highly conductive pitch based carbon fibers within the honeycomb structure.

2. Description of Related Art

Honeycomb structures are well known and widely used in many applications where a high strength and light weight material is required. The combined features of light weight and strength found in honeycomb structures makes them particularly well-suited for use in aircraft. Honeycomb structures have been made from a wide variety of materials including metals, such as aluminum. Composite materials made from resin impregnated fibers and papers have also been widely used in honeycomb structures. These materials have been particularly well-suited for use in aircraft due to their light weight, high strength and stiffness. In addition to light weight and high strength, non-metallic honeycomb structures are good insulators which find use in aircraft structures where their insulating properties are beneficial.

Although the insulating properties of non-metallic honeycombs are desirable in many instances, there are situations where it is desired to have high strength, lightweight materials which have a high thermal conductivity. For example, jet aircraft engines require a high degree of thermal transfer through the engine structure in order to maintain structural temperature loads at acceptable levels. Accordingly, the engine structure from the hot core to the outer nacelle must have high thermal conductivity while still being extremely strong and light weight.

Honeycomb structures made from aluminum are strong and have sufficient heat conductivity to transfer the necessary heat load from the hot core to the outer nacelle. However, aluminum core, in conjunction with graphite fiber reinforced composite skins, aluminum is subject to corrosion problems. Various glass fiber reinforced composite honeycomb structures and polyacrylonitrile (PAN) based carbon fiber reinforced composite materials have been suggested as potential substitutes for the aluminum honeycomb structures in jet aircraft engines. However, such non-metallic honeycomb structures are not suitable due to their poor thermal conductivity.

In view of the above, it would be desirable to provide non-metallic honeycomb structures which have increased thermal conductivity so that such structures could be used in applications where high heat transfer rates are required. It would further be desirable to provide such a high thermal conductivity non-metallic honeycomb structure wherein the desirable features of structural strength and light weight are maintained. It would also be desirable to provide such a high thermal conductivity non-metallic honeycomb structure having thermo-mechanical properties tailored to suit specific core loading scenarios.

SUMMARY OF THE INVENTION

In accordance with the present invention, a non-metallic honeycomb structure is provided which is lightweight, strong and exhibits a high degree of thermal conductivity. The present invention is based upon the discovery that highly conductive pitch based carbon fibers may be incorporated into non-metallic composite materials to provide high levels of thermal conductivity to the honeycomb structure.

In accordance with the present invention, a high thermal conductivity non-metallic honeycomb structure is provided wherein the structure includes a plurality of interconnected walls which define a plurality of interconnected honeycomb cells having a lengthwise direction which extends transversely relative to said walls and a thickness direction which extends parallel relative to the walls. The honeycomb walls include a plurality of non-metallic fibers having low thermal conductivity in combination with a plurality of non-metallic fibers having high thermal conductivity. The fibers are impregnated in a resin matrix.

As a feature of the present invention, the high thermal conductivity fibers may be oriented to extend substantially in the lengthwise direction of the honeycomb structure to provide directed transfer of heat transversely through the honeycomb. As another feature of the present invention, the high thermal conductivity fibers may be oriented to extend substantially in the thickness direction of the honeycomb to provide thermal transfer or conductance in the thickness direction, i.e., perpendicular to the lengthwise direction of the honeycomb.

As another feature of the present invention, the high thermal conductivity fibers may be oriented to extend at an angle relative to the lengthwise direction of the honeycomb structure to provide added structural strength to the structure in addition to controlled heat transfer in both the thickness and lengthwise directions.

As yet one more feature of the present invention, the cell walls of an exemplary honeycomb structure are formed from a plurality of non-metallic fiber-reinforced layers, at least one of which consists essentially of unidirectionally oriented high thermal conductivity fibers.

The use of pitch based carbon fibers to increase the conductivity of non-metallic honeycomb structures provides high strength, lightweight honeycomb structures which have a high degree of conductivity which makes them well-suited for a variety of uses where these three properties are required.

The above-described and many other features and attendant advantages of the present invention will become better understood by reference to the following detailed description when taken in conjunction with the accompanying drawings.

BRIEF DESCRIPTION OF THE DRAWINGS

FIG. 3 depicts a second preferred exemplary embodiment in accordance with the present invention wherein the high thermal conductivity pitch based carbon fibers are oriented in the lengthwise direction of the honeycomb structure to provide increased thermal transfer through the honeycomb structure in the lengthwise direction.

FIG. 4 is a detailed view of a portion of the honeycomb shown in FIG. 3.

FIG. 5 depicts a third preferred exemplary embodiment in accordance with the present invention wherein high thermal conductivity pitch based carbon fibers are arranged at angles of plus and minus 45° relative to the lengthwise direction to provide increased structural strength, as well as increased multi-directional heat transfer through the honeycomb structure.

FIG. 6 is a detailed view of a portion of the honeycomb shown in FIG. 5.

FIG. 10 depicts a preferred exemplary honeycomb structure formed from a plurality of the laminar honeycomb ribbons of the type shown in FIG. 8.

FIG. 11 depicts the preferred exemplary non-metallic cell wall of FIG. 8 with exterior non-porous fabric layers laminated thereto.

DESCRIPTION OF THE PREFERRED EMBODIMENTS

The present invention involves the discovery that pitch based carbon fibers may be incorporated into non-metallic honeycomb structures to increase the thermal conductivity of such honeycomb structures. Further, it was discovered that the thermal conductance or transfer of heat through the honeycomb structure can be controlled and directed by orienting the pitch based carbon fibers in selected directions.

The present invention has wide application to increasing the thermal conductivity of non-metallic honeycomb structures used in many different applications. The present invention is particularly well-suited for use in jet aircraft engines where heat transfer from the hot core to outer nacelles is desired and wherein strong, lightweight structures are desired. Although the present invention is particularly well-suited for such aircraft type applications, it will be recognized by those skilled in the art that the increase in thermal conductivity provided by the present invention may be beneficially used to increase and control the thermal conductivity of non-metallic honeycomb structures used in any number of situations where strength, light weight and high heat transfer is required.

The present invention is particularly well-suited for increasing the thermal conductivity of honeycomb structures which are made from resin impregnated polyacrylonitrile (PAN) based carbon fibers. The invention may also be used to increase and control the thermal conductivity of other non-metallic honeycomb structures such as resin-impregnated glass fibers, resin impregnated polyaramide fibers and resin impregnated ceramic fibers. The resins used in these types of composite materials are typically thermoset or thermoplastic polymers. Examples of suitable polymers include phenolic resins, polyimide resins and epoxy resins.

The thermal conductivity of PAN, glass and ceramic fibers is typically less than 100 watts/m° K. Non-metallic fibers having thermal conductivities in this range are considered to have low thermal conductivity. The resins in which these fibers are impregnated to make the honeycomb structure also have low thermal conductivity so that the resulting honeycomb structure will have an overall thermal conductivity which falls within this relatively low range.

In accordance with the present invention, the above-described low thermal conductivity honeycomb structures are converted into high thermal conductivity honeycomb structures utilizing pitch based carbon fibers. Pitch based carbon fibers have a high thermal conductivity which is typically on the order of 200 watts/m° K to about 1200 watts/m° K. As will be described in detail below, pitch based carbon fibers may be incorporated into the honeycomb structure in amounts ranging from about 1 weight percent to about 90 weight percent in order to provide a high thermal conductivity honeycomb in which the direction of thermal transfer may be controlled if desired.

Figure 1:
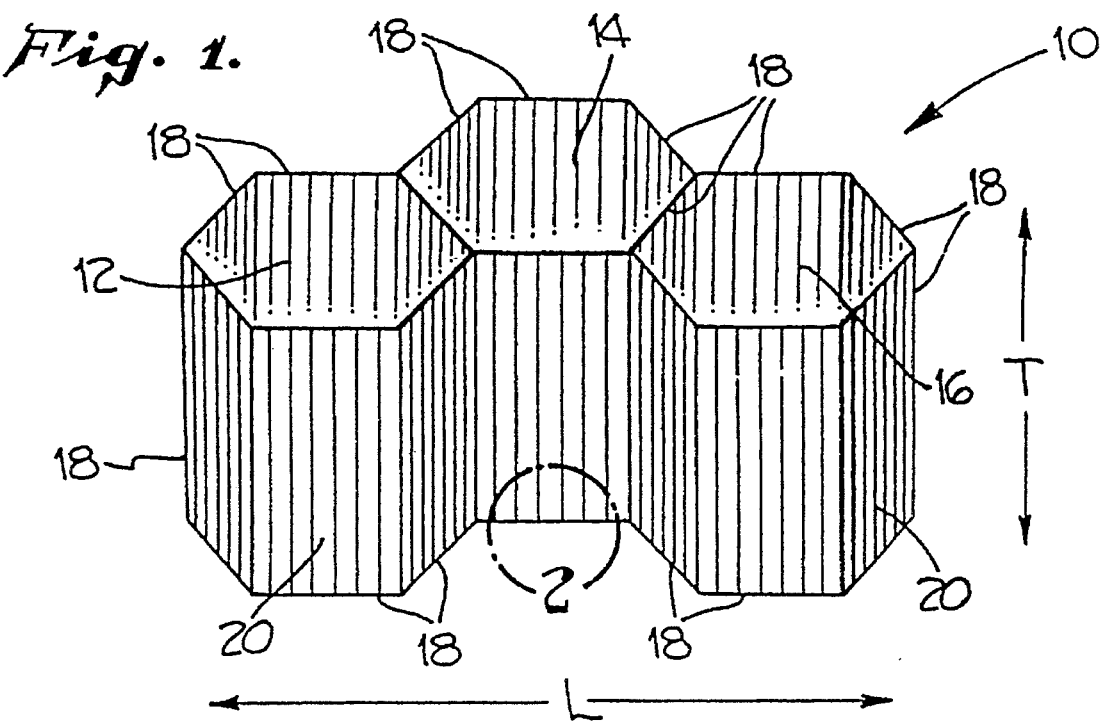
FIG. 1 depicts a preferred exemplary non-metallic honeycomb structure in accordance with the present invention wherein pitch based carbon fibers having high thermal conductivity are oriented in the thickness direction of the honeycomb structure to provide increased thermal transfer through the honeycomb in the thickness direction.

Referring to FIG. 1, a small portion of a preferred exemplary honeycomb structure is shown generally at 10. The honeycomb structure 10 includes three interconnected honeycomb cells 12, 14 and 16. As is well known, honeycomb structures typically include hundreds and thousands of such interconnected honeycomb cells. For purposes of illustration, only three cells are shown with it being understood that the remainder of the interconnected honeycomb cells which typically make up a honeycomb structure are not shown.

The honeycomb cells 12, 14 and 16 are formed by a plurality of interconnected walls 18. The honeycomb cells have a lengthwise direction which extends transversely relative to the honeycomb walls 18 and is represented by L in FIG. 1. The honeycomb cells also have a thickness direction which extends parallel relative to the walls 18 and is represented by T in FIG. 1. In accordance with the present invention, a plurality of pitch based carbon fibers are impregnated in the resin matrix so that they extend substantially in the thickness direction T. The orientation of the pitch based carbon fibers in the honeycomb structure 10 are represented by vertical lines 20 which extend parallel to the T direction. Orientation of the pitch based fibers 20 in a direction substantially parallel to the thickness direction provides for increased thermal conductance through the honeycomb structure and provides directed thermal transfer in the T direction.

Figure 2:
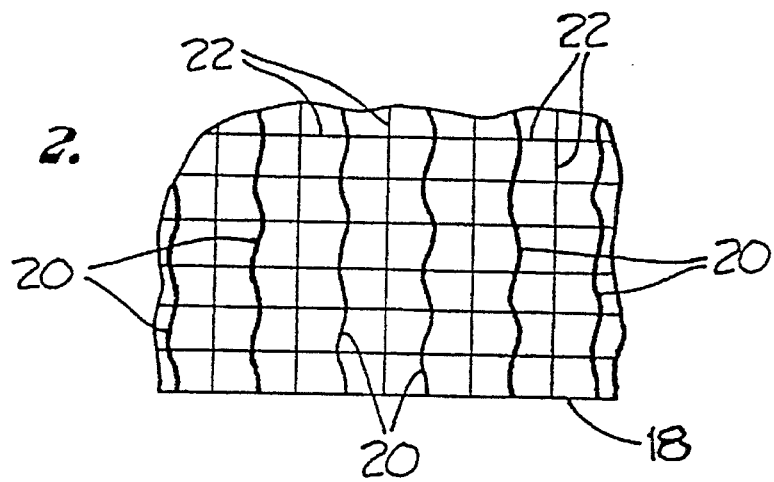
FIG. 2 is a detailed view of a portion of the honeycomb structure shown in FIG. 1.

A portion of the cell wall 18 is shown in detail in FIG. 2. The cell wall 18 is made up of a fabric layer and cured resin. The fabric layer includes non-metallic fibers 22 which are shown in a conventional plain weave pattern. The fibers 22 can be any of the previously mentioned low conductivity fibers. PAN-based carbon fibers are preferred. The PAN-based carbon fibers may be woven in any of the conventional weave patterns with from about 500 to 3000 filaments per tow being preferred. The individual filaments used in each of the tows preferably have diameters in the range of between about 5 to 9 microns.

The particular weave pattern, filament size and tow size may be varied widely depending upon the structural strength and weight required for the honeycomb structure. The formation of honeycomb structures from resin impregnated PAN-based carbon fibers is well known in the art. In this first preferred embodiment, the pitch based carbon fibers 20 are interwoven into the low thermal conductivity fibers 22 to provide a unidirectional pattern of high thermal conductivity pitch based carbon fibers.

The pitch based carbon fibers can be any of the pitch based carbon fibers which are commercially available. Such fibers are available from companies such as AMOCO under the trade name THORNEL CARBON FIBER. The pitch based carbon fibers should have a thermal conductivity on the order of 200 watts/m° K to about 1200 watts/m° K. The individual pitch based carbon fibers typically have diameters in the range of between about 7 microns to about 11 microns with the tows which are woven into the fabric having from 500 to 2000 filaments each. Pitch based fibers identified as P120 are preferred with P75, K950 and K1100 fibers also being acceptable.

The amount of pitch based carbon fiber which is woven into the PAN-based carbon fiber fabric may be varied depending upon the degree of thermal conductance required. Typically, from about 1 weight percent to about 90 weight percent of pitch based carbon fiber (based on the total weight of the cured composite material) provides substantial increases in thermal conductivity while still maintaining the high strength and light weight characteristics of the composite material.

A second preferred honeycomb structure is shown at 30 in FIG. 3. Again, only three cells 32, 34 and 36 of a much larger honeycomb structure are shown. The honeycomb structure is basically the same as the non-metallic honeycomb structure shown in FIGS. 1 and 2 except that the pitch based carbon fibers are oriented in the lengthwise direction of the honeycomb structure 30. The orientation of the pitch based carbon fibers is represented by lines 38. In this embodiment, heat transfer through the honeycomb structure 30 is maximized in the L-direction. As is apparent from the structure shown in FIGS. 1 and 3, the present invention provides the capability of controlling heat conductance through honeycomb structures in either the thickness or lengthwise directions.

A detailed view of one of the honeycomb cell walls 40 of FIG. 3 is shown in FIG. 4. The cell walls 40, like previously described cell walls 18 include a woven fabric of PAN based carbon fibers 42 embedded in a polyester resin.

The high thermal conductivity pitch-based carbon fibers 38 are oriented so that during honeycomb fabrication, the fibers 38 extend uniformly in the lengthwise direction of the honeycomb structure. If desired, the same woven material which includes the high conductivity pitch-based carbon fibers may be used in fabricating the honeycomb structure of FIG. 1 or FIG. 3. In the first embodiment, the impregnated fabric layer is oriented during the fabrication process so that the pitch based carbon fibers 20 will extend in the thickness direction in the final cured honeycomb structure. The same fabric can be rotated 90° during the fabrication process so that the same pitch-based fibers extend in the lengthwise direction as shown in FIGS. 3 and 4.

A third preferred exemplary honeycomb structure in accordance with the present invention is shown generally at 50 in FIG. 5. The three honeycomb cells 52, 54 and 56, like the previously described embodiments, are only a small portion which is representative of an overall honeycomb structure comprising hundreds or thousands of cells. The honeycomb structure 50 is made in accordance with the same conventional fabrication procedures used to fabricate the first and second honeycomb embodiments.

The principal difference between this third honeycomb embodiment and the previous embodiments is that the fabric used to form the cell walls 58 includes pitch-based carbon fibers which are oriented at angles of plus or minus 45° relative to the lengthwise direction L and thickness direction T. The orientation of the pitch-based fibers are represented by lines 60. A detailed view of the weave pattern for the resin impregnated honeycomb wall is shown in FIG. 6. The weave pattern for the polyacrylonitrile based carbon fibers is the same as in the previous embodiments. However, as previously mentioned, a wide variety of weave patterns using a variety of non-metallic low thermal conductivity fibers may be used. In this embodiment, the pitch-based carbon fibers are oriented in a two directional weave pattern to provide heat transfer in both the lengthwise and thickness directions of the honeycomb structure.

The plus/minus 45° orientation of pitch fibers shown in FIG. 5 is a preferred orientation. Other plus/minus fiber orientation angles are possible in accordance with the present invention. For example, plus/minus angles ranging from 0 to 90 degrees are possible to provide a variety of different combinations of structural strengths and thermal transfer properties to the honeycomb structure. Also, the pitch based fibers may all be oriented in a plus angle direction in the 0 to 90 degrees range or the fibers may all be oriented in a minus angle in 0 to 90 degree range. Mixtures of varying amounts of plus and minus angled fibers may be used to provide even further control of the direction of heat transfer through the honeycomb structure.

Figure 7:
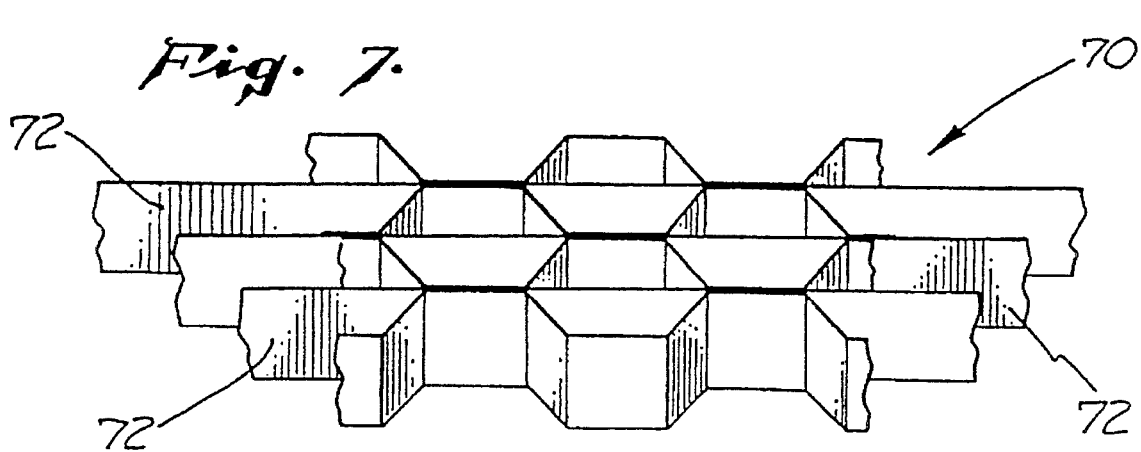
FIG. 7 depicts a fourth preferred exemplary embodiment which is the same as the honeycomb structure depicted in FIG. 1 except that flat reinforcing sheets are placed between the honeycomb corrugations.

A fourth preferred exemplary honeycomb structure is shown at 70 in FIG. 7. The honeycomb 70 is the same as the honeycomb structure shown in FIG. 1 except that flat sheets 72 are located in between the corrugated sheets which form the honeycomb structure. The flat sheets 72 extend through the middle of the cell and provides additional reinforcement and heat transfer when desired. The fabric used to form the flat sheets 70 may be selected from any of the non-metallic composite materials which are used to form the walls of the honeycomb.

Figure 8:
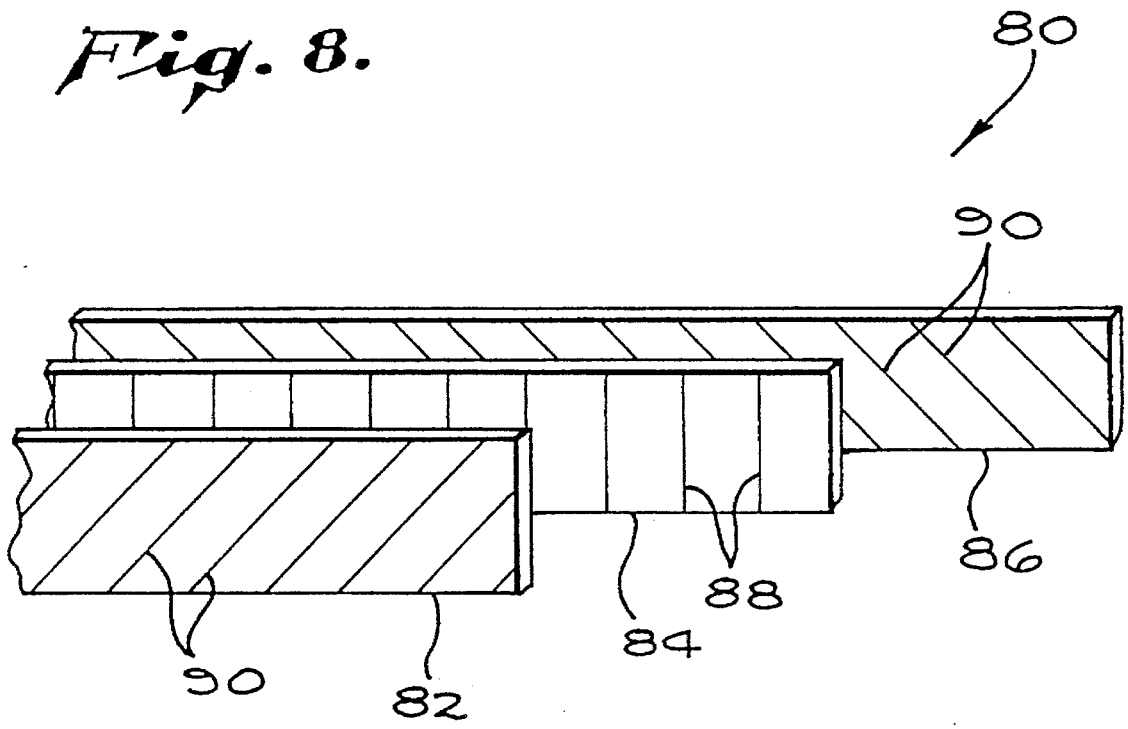
FIG. 8 depicts an exploded view of the cell wall of a fifth preferred exemplary embodiment in accordance with the present invention wherein the cell walls are formed from a plurality of unidirectional non-metallic fabric layers impregnated within a resin matrix.

An exemplary cell wall of a fifth preferred exemplary honeycomb structure is shown generally at 80 in FIG. 8. Unlike the previously described cell walls of FIGS. 1–6, cell wall 80 is formed from a plurality of non-metallic unidirectional fabric layers 82, 84, and 86. Layers 82 and 86 consist essentially of unidirectionally oriented PAN-based low thermally conductive carbon fibers. Layer 4 consists essentially of unidirectionally oriented pitch based high thermally conductive carbon fibers. Preferably, fabric layers 82, 84 and 86 are formed from non-woven unidirectional tapes.

In fabric layers 82 and 86, the PAN-based carbon fibers are oriented at angles of about plus and minus 45°, respectively, relative to the lengthwise direction L and thickness direction T. In fabric layer 84, the pitch based carbon fibers are oriented in the thickness direction T. The orientation of the pitch based carbon fibers is represented by lines 88. The orientation of the PAN based carbon fibers of layers 82 and 86 are represented by lines 90 and 92.

Preferably, the unidirectionally oriented carbon fibers of each fabric layer 82, 84 and 86 are secured in place relative to other carbon fibers of the same layer using conventional bonding or stitching means (not shown).

Figure 9:
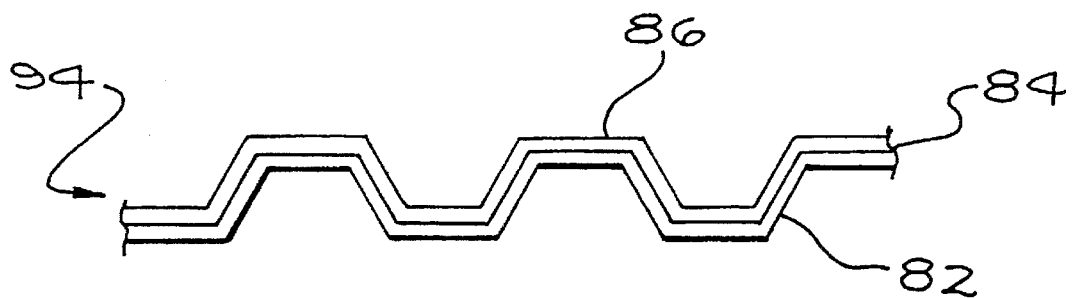
FIG. 9 depicts a preferred exemplary corrugated laminar honeycomb ribbon formed from a non-metallic cell wall as shown in FIG. 8.

As best shown in FIGS. 9 and 10, fabric layers 82, 84 and 86 are formed into corrugated honeycomb ribbons 94 which comprise the cell walls 80 of honeycomb cells 96, 98, and 100. In forming the honeycomb ribbons, a resin matrix is used to bond the obverse sides of adjacent fabric layers together. Thereafter, the honeycomb ribbons are molded into a preferred shape and cured. Preferably, fabric layers 82, 84 and 86 are preimpregnated with a suitable resin before lamination, molding and curing. Once the corrugated ribbons 94 are formed, the obverse sides of adjacent corrugated ribbons 94 are bonded using a preferred resin to form the honeycomb structure.

As with the embodiment shown in FIGS. 1 and 2, this fifth preferred embodiment maximizes heat transfer through the honeycomb structure 80 in the "T" direction. However, with the PAN-based carbon fibers oriented diagonally relative to the lengthwise direction L and thickness direction T, this embodiment demonstrates different mechanical properties including improved shear strength relative to the embodiment shown in FIGS. 1 and 2.

While the plus and minus 45° orientation of PAN-based fibers of fabric layers 82 and 84 is provides for a honeycomb structure more resistant to shear stresses, other PAN-based carbon fabrics having different fiber orientations are possible in accordance with the present invention. For example, plus and/or minus angles ranging from 0° to 90° are possible to provide a variety of different combinations of structural strengths.

The heat transfer characteristics of the embodiment shown in FIGS. 8–10 similarly may be changed by utilizing unidirectional fabrics with pitch based carbon fibers unidirectionally oriented in other directions. For example, by providing a fabric with the pitch based fibers oriented in the manner shown in FIG. 4, heat transfer through the honeycomb will be maximized in the "L" direction.

Because the pitch based carbon fibers are not integrally formed in a fabric layer comprising PAN-based carbon fibers, a number of different orientations of pitch based fibers relative to PAN-based fibers are possible. Accordingly, a honeycomb structure can be formed to have thermomechanical properties tailored to suit specific core loading scenarios with each application determining the number of layers, the constituents and orientation of each layer, and the positioning of each layer relative to other layers.

In applications where the honeycomb structure is preferably substantially non-porous, a non-porous nonmetallic layer 102 may be laminated to the exterior surface of each honeycomb ribbon before curing and molding as best shown in FIG. 11. A preferred exterior laminate is composed of a matting comprising randomly oriented low thermally conductive PAN-based carbon fibers. Upon impregnation of the matting in a resin matrix and curing, the carbon fiber matting is substantially non-porous thereby providing a substantially non-porous honeycomb structure. Other non-metallic non-porous exterior laminates which may be used in accordance with the present invention are well known in the art and include polymer films and dry fiber mats.

Examples of practice are as follows:

EXAMPLE 1

A honeycomb structure having walls with the weave pattern shown in FIG. 1 was fabricated. The fabric had the specifications set forth in Table 1.

TABLE 1

| SPECIFICATION | VALUE |
| --- | --- |
| FIBER TYPE | |
| WARP | T300 1K |
| FILL | T300 1K:P120 2K |
| FABRIC CONSTRUCTION | HYBRID PLAIN WEAVE |
| YARN COUNT | |
| WARP (PER INCH) | 22 |
| FILL (PER INCH) | 15 (T300):7.5 (P120) |
| FABRIC AREAL WEIGHT (CALCULATED) | |
| G/SQ M | 192 |
| OZ/SQ YD | 5.65 |

The T300 PAN fibers were obtained from Toray. The fabric was impregnated with 35 weight percent polyamic acid resin and formed into the honeycomb structure shown in FIG. 1 by conventional fabrication techniques. The resulting honeycomb structure had 36 weight percent pitch based carbon fiber (P120) and had a thermal conductivity which was significantly greater in the "T" direction than an identical honeycomb structure made without the P120 fibers. The structural strength of the honeycomb made with P120 fibers was equivalent to the structural strength of the identical honeycomb structure made without the P120 fibers.

EXAMPLE 2

A honeycomb structure having walls with the weave pattern shown in FIG. 5 was fabricated using the same fabric and resin used in Example 1. The resulting honeycomb structure had a thermal conductivity which was significantly greater in the T and L direction than an identical honeycomb structure made without the incorporation of the pitch based carbon fibers running at plus and minus 45°. The structural strength of the honeycomb structure with the pitch based fibers was equivalent to the identical honeycomb structure without pitch based fibers.

EXAMPLE 3

A honeycomb structure having the configuration shown in FIG. 7 was fabricated according to the same procedure used in Example 1. The fabric layer which was used to form the flat reinforcement layer (72 in FIG. 7) had the specification set forth in Table 2.

TABLE 2

| SPECIFICATION | VALUE |
| --- | --- |
| FIBER TYPE | |
| WARP | T300 3K |
| FILL | T300 1K:P120 2K |
| FABRIC CONSTRUCTION | HYBRID PLAIN WEAVE |
| YARN COUNT | |
| WARP (PER INCH) | 12.5 |
| FILL (PER INCH) | 5.75 (T300):7.5 (P120) |
| FABRIC AREAL WEIGHT (CALCULATED) | |
| G/SQ M | 187 |
| OZ/SQ YD | 5.52 |

The fabric used to form the honeycomb walls included T300–3K, Style 282 PAN with 10 weight percent P120 pitch carbon fiber. The resulting honeycomb structure had a thermal conductivity which was significantly greater than an identical honeycomb structure made without the incorporation of the pitch based carbon fibers.

Having thus described exemplary embodiments of the present invention, it will be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A high thermal conductivity non-metallic honeycomb structure comprising:

a plurality of interconnected walls which define a plurality of interconnected honeycomb cells having a lengthwise direction which extends transversely relative to said walls and a thickness direction which extends parallel relative to said walls, said call walls comprising:

a first low thermal conductivity structural layer comprising a plurality of non-metallic fibers having low thermal conductivity, said first structural layer having an interior and an exterior surface;

a second low thermal conductivity structural layer comprising a plurality of non-metallic fibers having low thermal conductivity, said second structural layer having an interior and an exterior surface;

a thermally conductive layer sandwiched between the interior surfaces of said first and second structural layers, said thermally conductive layer comprising a plurality of non-metallic fibers having high thermal conductivity to provide directionally controlled heat conductance through said honeycomb structure;

a first non-porous and non-metallic layer which is laminated to the exterior surface of said first structural layer; and a second non-porous and non-metallic layer which is laminated to the exterior surface of said second structural layer.

2. A high thermal conductivity non-metallic honeycomb structure according to claim 1 wherein said first low thermal conductivity structural layer comprises unidirectional non-metallic fibers which are oriented at an angle of plus 45° relative to said lengthwise direction.

3. A high thermal conductivity non-metallic honeycomb structure according to claim 1 wherein said second low thermal conductivity structural layer comprises unidirectional non-metallic fibers which are oriented at an angle of minus 45° relative to said lengthwise direction.

4. A high thermal conductivity non-metallic honeycomb structure according to claim 1 wherein said thermally conductive layer comprises unidirectional non-metallic fibers which are oriented at an angle of plus 60° relative to said thickness direction.

5. A thermally conductive honeycomb structure according to claim 1 wherein said high thermal conductivity fibers consist essentially of pitch based carbon.

6. A thermally conductive honeycomb structure according to claim 1 wherein said low thermal conductivity fibers are selected from the group consisting of polyacrylonitrile based carbon fibers, glass fibers, polyaramide fibers and ceramic fibers.

7. A thermally conductive honeycomb structure according to claim 1 wherein said low thermal conductivity fibers consist essentially of polyacrylonitrile based carbon.

8. A thermally conductive honeycomb structure according to claim 1 wherein said first and second non-porous and non-metallic layers each comprise randomly oriented low thermally conductive PAN-based carbon fibers which are impregnated in a resin matrix.

9. A high thermal conductivity non-metallic honeycomb structure according to claim 2 wherein said second low thermal conductivity structural layer comprises unidirectional non-metallic fibers which are oriented at an angle of minus 45° relative to said lengthwise direction.

10. A high thermal conductivity non-metallic honeycomb structure according to claim 9 wherein said thermally conductive layer comprises unidirectional non-metallic fibers which are oriented at an angle of plus 60° relative to said thickness direction.

* * * * *